(12) United States Patent
Wan et al.

(10) Patent No.: US 10,413,292 B2
(45) Date of Patent: Sep. 17, 2019

(54) LINEAR STAPLER WITH A MULTI-FUNCTIONAL RETAINING PIN SUBASSEMBLY

(71) Applicant: Ethicon Endo-Surgery, Inc., Cincinnati, OH (US)

(72) Inventors: Shan Wan, Mason, OH (US); Xiangchun Hong, Shanghai (CN); Lian Xu, Shanghai (CN); Wei Sun, Shanghai (CN)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 15/589,390

(22) Filed: May 8, 2017

(65) Prior Publication Data

US 2017/0238927 A1    Aug. 24, 2017

Related U.S. Application Data

(63) Continuation of application No. 14/126,477, filed as application No. PCT/US2012/041307 on Jun. 7, 2012, now abandoned.

(30) Foreign Application Priority Data

Jun. 21, 2011 (CN) .......................... 2011 1 0189676

(51) Int. Cl.
*A61B 17/072* (2006.01)

(52) U.S. Cl.
CPC .. *A61B 17/072* (2013.01); *A61B 2017/07271* (2013.01); *A61B 2017/07278* (2013.01)

(58) Field of Classification Search
CPC .................................................... A61B 17/072
USPC ........................................................ 227/175.1
See application file for complete search history.

(56) References Cited

U.S. PATENT DOCUMENTS

| 3,692,224 A * | 9/1972 | Astafiev ............... A61B 17/072 227/19 |
| 5,071,052 A * | 12/1991 | Rodak .................. A61B 17/072 227/124 |
| 5,579,978 A | 12/1996 | Green |
| 5,810,240 A | 9/1998 | Robertson |
| 6,817,508 B1 | 11/2004 | Racenet |
| 6,988,650 B2 * | 1/2006 | Schwemberger .... A61B 17/072 227/176.1 |

(Continued)

FOREIGN PATENT DOCUMENTS

| CN | 1669533 A | 9/2005 |
| CN | 101856251 A | 10/2010 |
| EP | 0514139 A2 | 11/1992 |

(Continued)

*Primary Examiner* — Andrew M Tecco
*Assistant Examiner* — Eyamindae C Jallow (57) ABSTRACT

The present invention provides a linear stapler having a multi-functional retaining pin subassembly. The linear stapler comprises a handle stem connecting an anvil to a handle, and the retaining pin subassembly is movably supported on the handle stem and comprises a connecting cover having a retaining pin extending from the connecting cover. The present invention also provides a multi-functional retaining pin subassembly. The retaining pin subassembly can achieve cartridge alignment and tissue retention during the firing of the stapler and protect tissue from unintended damage.

8 Claims, 9 Drawing Sheets

(56) References Cited

U.S. PATENT DOCUMENTS 8,424,738 B2 * 4/2013 Kasvikis .............. A61B 17/072
　　　　　　　　　　　　　　　　　　227/176.1

FOREIGN PATENT DOCUMENTS

| EP | 1324707 B | 9/2003 |
| EP | 1550410 A2 | 7/2005 |
| GB | 2141066 B | 12/1984 |
| JP | 2004-528859 A | 9/2004 |

* cited by examiner

Fig. 9

LINEAR STAPLER WITH A MULTI-FUNCTIONAL RETAINING PIN SUBASSEMBLY

CROSS REFERENCE TO RELATED APPLICATIONS

This application is a continuation of U.S. patent application Ser. No. 14/126,477, filed on Mar. 12, 2014, which claims priority to International Application No. PCT/US2012/041307, filed on Jun. 7, 2012, which claims priority to Chinese Application No. 201110189676.6, filed on Jun. 21, 2011, the entire contents of each are hereby incorporated by reference herein in their entirety.

FIELD OF THE INVENTION

The present invention generally relates to a surgical stapler, and more particularly, to a linear stapler having a multi-functional retaining pin subassembly.

BACKGROUND OF THE INVENTION

More and more surgeons tend to use surgical staples, rather than conventional sutures since the use of surgical staples and surgical staplers can make many complex procedures much simpler and thereby reduce operation time. Many types of surgical staplers have been devised for different procedures, including linear staplers.

Over time, linear surgical staplers have evolved with significant improvements. These instruments generally include a pair of jaws cooperating with each other and supporting anvil and staple cartridge, respectively. The instruments also include a driver within the cartridge casing that pushes all of the staples out simultaneously against the anvil to form the staples into a generally B-shape, suturing tissue together. In addition, these instruments include approximation mechanisms that allow the cartridge housing and anvil to move relative to each other to accept tissue therebetween. Finally, the instruments include a handle and an activating "firing" mechanism. A surgeon moves the driver forward to form the staples against the anvil by actuating the firing mechanism with a firing trigger.

Although such instruments can staple tissue well, there is still room for improvement. For example, the current linear staplers often use left and right handle plates in the form of frame plate to connect the jaws to the handle and a driving mechanism is received in a space formed by the handle plates. Since the space formed by the handle plates is open, tissue is prone to be damaged for being trapped in the space during the insertion and firing of the instruments. U.S. Pat. No. 4,527,724 discloses a disposable linear stapler, in which a separate spacer is provided between the left and right handle plates. The spacer closes the space to some extent. However, as a large number of components usually means higher product cost and lower reliability for medical instruments, that instrument is not preferable.

For another example, a conventional alignment and retaining pin takes the form of a slim pin/wire extending from a position near the proximate end (i.e., the end with the handle) of the instruments up to its distal end (opposite end to the proximate end) to facilitate the manipulation by a surgeon. As a result, this kind of slim pin/wire with a long length inevitably limits the strength and robustness of the instrument.

Besides, it is also desirable to enhance the cleanability of a disposable and reusable linear stapler while maintaining its performance to make the cleansing work (i.e. assembly, disassembly, cleaning, sterilization and the like) easier.

The present invention is directed to improvements in one or more aspects as set forth above.

SUMMARY OF THE INVENTION

The present invention provides a linear stapler comprising: a body for supporting a cartridge having one or more surgical staples, wherein the body has an driver for acting on the cartridge to drive the surgical staples therefrom; and wherein the body has a handle stem supporting an anvil against which tissue can be pressed by the cartridge for stapling; and a retaining pin subassembly movably supported on the handle stem, wherein the retaining pin subassembly comprises a connecting cover having a retaining pin extending therefrom, the connecting cover being capable of covering an opening of the handle stem.

The retaining pin can be used for alignment. In one embodiment, the retaining pin extends in a direction substantially parallel to the direction of slide of the connecting cover but is off set upward therefrom 1 cm to 10 cm. In another embodiment, the retaining pin extending in a direction aligned with the direction of slide of the connecting cover in the linear stapler.

In one embodiment, the handle stem can be a handle plate.

According to one embodiment, the connecting cover includes a base for the retaining pin.

According to one embodiment, the connecting cover is provided at its proximate end a push lever extending at an angle from the sliding direction of the connecting cover (for example, the angle can be an upwardly angle), and the push lever can be manipulated manually.

According to one embodiment, the connecting cover is made of a metal material.

According to one embodiment, a plurality of legs (e.g., arranged as pairs of legs) extends downwardly from the connecting cover. Furthermore, the plurality of legs have bumps extending inwardly (e.g., such as when the legs have inward facing surfaces facing across the width of the connecting cover "inner surfaces" and the bumps are on the legs' inner surfaces) facing each other, the connecting cover snap fits on sides of the handle plate via the bumps.

According to one embodiment, the legs are elastic.

According to one embodiment, the handle stem includes left and right handle plates.

According to one embodiment, the retaining pin subassembly is undetachably connected to the handle stem via a locking device.

The present invention also provides a multi-functional retaining pin subassembly for use in a linear stapler, the linear stapler comprises a handle stem connecting an anvil to a handle, and wherein the retaining pin subassembly is movably supported on the handle stem and comprises a connecting cover having a retaining pin extending therefrom, the connecting cover being capable of covering an opening of the handle stem.

The retaining pin subassembly according to the present invention may serve multiple functions. For example, it can be an alignment and retaining pin to enhance the disposable or reusable cartridge alignment to ensure proper staple firing. And the retaining pin can also serve its retaining function to retain tissue between the anvil and cartridge during the staple firing. Also, the connecting cover may act as a top cover to reduce the openness of the instrument and avoid the possible tissue damage during the insertion and firing of the instrument. Meanwhile, as a structural part, the connecting cover in its shape and material (e.g., plate shape and made of steel) advantageously improves the strength and robustness of the retaining pin subassembly. Preferably, the small bumps on the connecting cover interacting with the retaining pin guide can provide tactile feedback to surgeons that the retaining pin is in the right position.

Compared with the prior art, the present invention reduces the number of components, improves the reliability of the instrument, and makes it easy to clean and sterilize without compromising its performance by forming a retaining pin subassembly with a connecting cover and a retaining pin.

BRIEF DESCRIPTION OF THE DRAWINGS

Other features and advantages of the present invention will become apparent from the following detailed description when viewed in conjunction with the accompanying drawings, which set forth certain exemplary but non-limiting embodiments of the invention.

DESCRIPTION OF THE PREFERRED EMBODIMENTS

In the following, certain exemplary embodiments will be described in detail with reference to the accompanying drawings, in which like numeral signs are used for like components.

Figure 1:
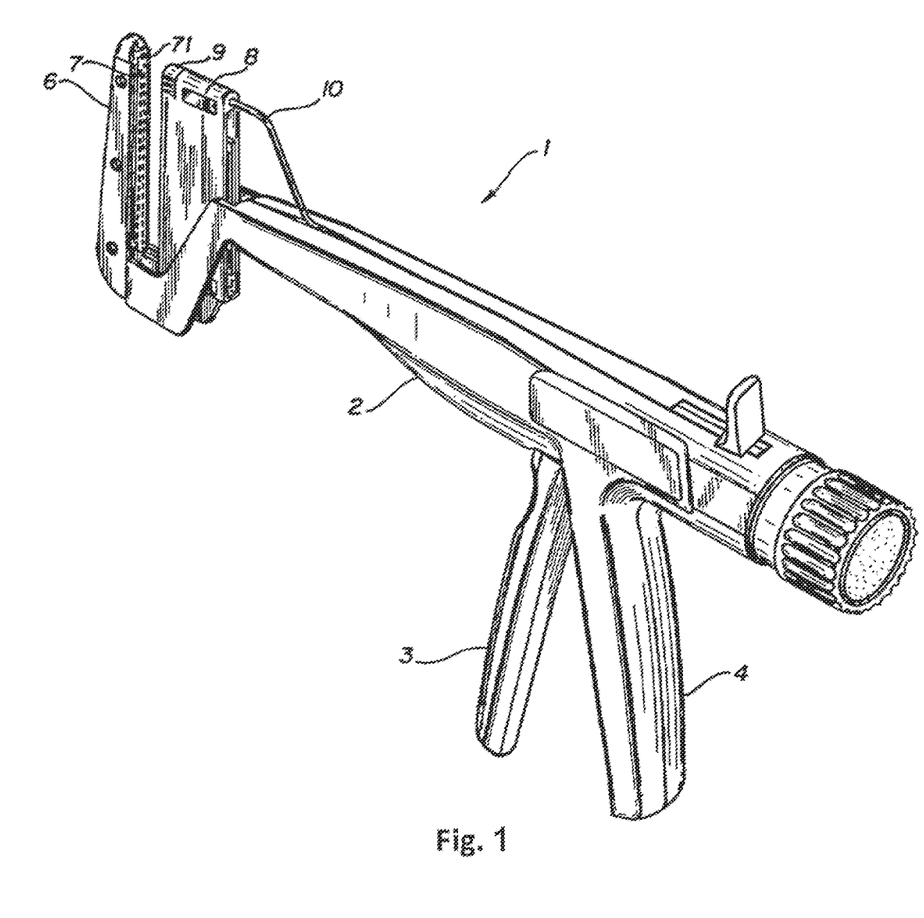
FIG. 1 is a perspective view of a linear stapler in prior art.

Referring to drawings, FIG. 1 illustrates an exemplary linear stapler 1 in prior art schematically showing the basic construct thereof. The linear stapler 1 includes a body 2 for supporting a cartridge 9 with one or more surgical stapler. The body 2 also has a driver 15 acting upon the cartridge 9 to expel the surgical stapler therefrom. Specifically, as shown, the body 2 includes a handle 4 and a trigger 3 pivotally connected with the handle 4 at a proximate end. A fixed jaw 6 supporting an anvil 7 and a movable jaw 8 including a cartridge 9 are provided at a distal end of the linear stapler 1. The cartridge 9 is removably inserted in the linear stapler so that it can be removed after use.

Figure 2:
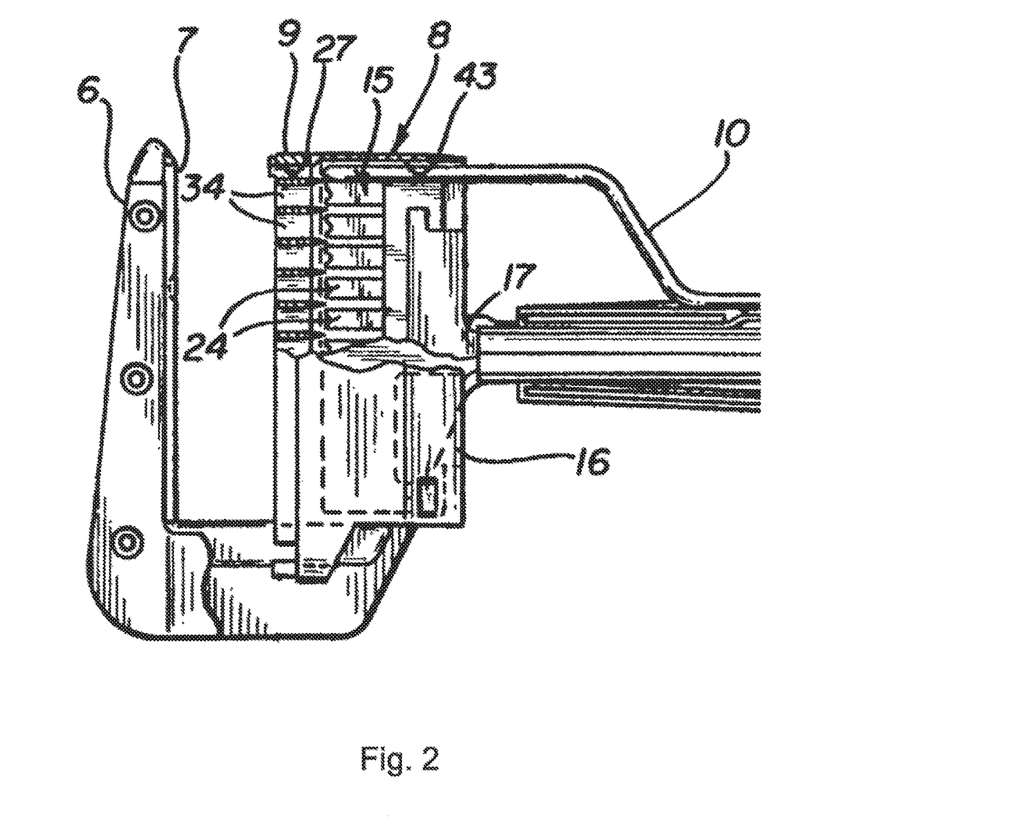
FIG. 2 is a partially-cut-out view of some components of the linear stapler shown in FIG. 1.

A cartridge/driver assembly, i.e. the movable jaw 8, comprises the cartridge 9, a staple driver 15, a casing 16, a driver rod 17 and the like. The cartridge 9 can constitute an integral, one piece member (typically made with molded plastic, although other material can be used) and can be reused by reloading staples. The linear stapler can be reused by removing a spent empty cartridge and loading with a new cartridge with staples. "Plastic member" used herein refers to a member formed of a plastic material of adequate strength, suitable for use in a surgical environment, and capable of sterilization by one or more known accepted methods. The cartridge 9 contains a plurality of staple-containing slots 34 for rows of staples. A driver 15 is disposed in the casing 16 and behind the cartridge 9, for expelling all the staples simultaneously out of the staple-containing slots 34. For example, the driver 15 can be a mechanical member having a plurality of tips 24 aligned with the surgical staples contained in the staple-containing slots 34 for pushing the staples. It can also be a balloon hydraulically or pneumatically actuated. The driver rod 17 may be a metal member having elongate shank with one distal end contained in the casing 16 and interacting with the driver 15 and one proximate end engaged with the trigger 3. The trigger 3 interacts with the driver rod 17 to push it and thus the driver 15 distally to fire staples when the trigger 3 is pulled towards the handle 4.

The anvil 7 has a staple-shaping surface for forming the staples into a generally B-shape in order to achieve tissue engagement. Once tissue to be stapled is positioned between the anvil 7 and cartridge 9, the trigger 3 may be actuated by a surgeon to fire staples towards the staple-forming surface of the anvil 7 to form the staples, thereby stapling the tissue.

In addition, the body 2 further includes a handle stem 20 supporting the anvil 7. The fixed jaw 6 is connected to the handle 4 via the handle stem 20 having handle plates 2 each in the form of a frame plate. The handle stem 20 can include left and right handle plates, for example. They typically are made of metal and constitute the "main frame" of the linear stapler. Said driver rod 17 is located between the left and right handle plates and capable of moving distally under the actuation of the trigger 3 as mentioned above.

The linear stapler 1 further comprises a multi-functional retaining pin subassembly 10 supported on the handle stem 20.

Figure 3:
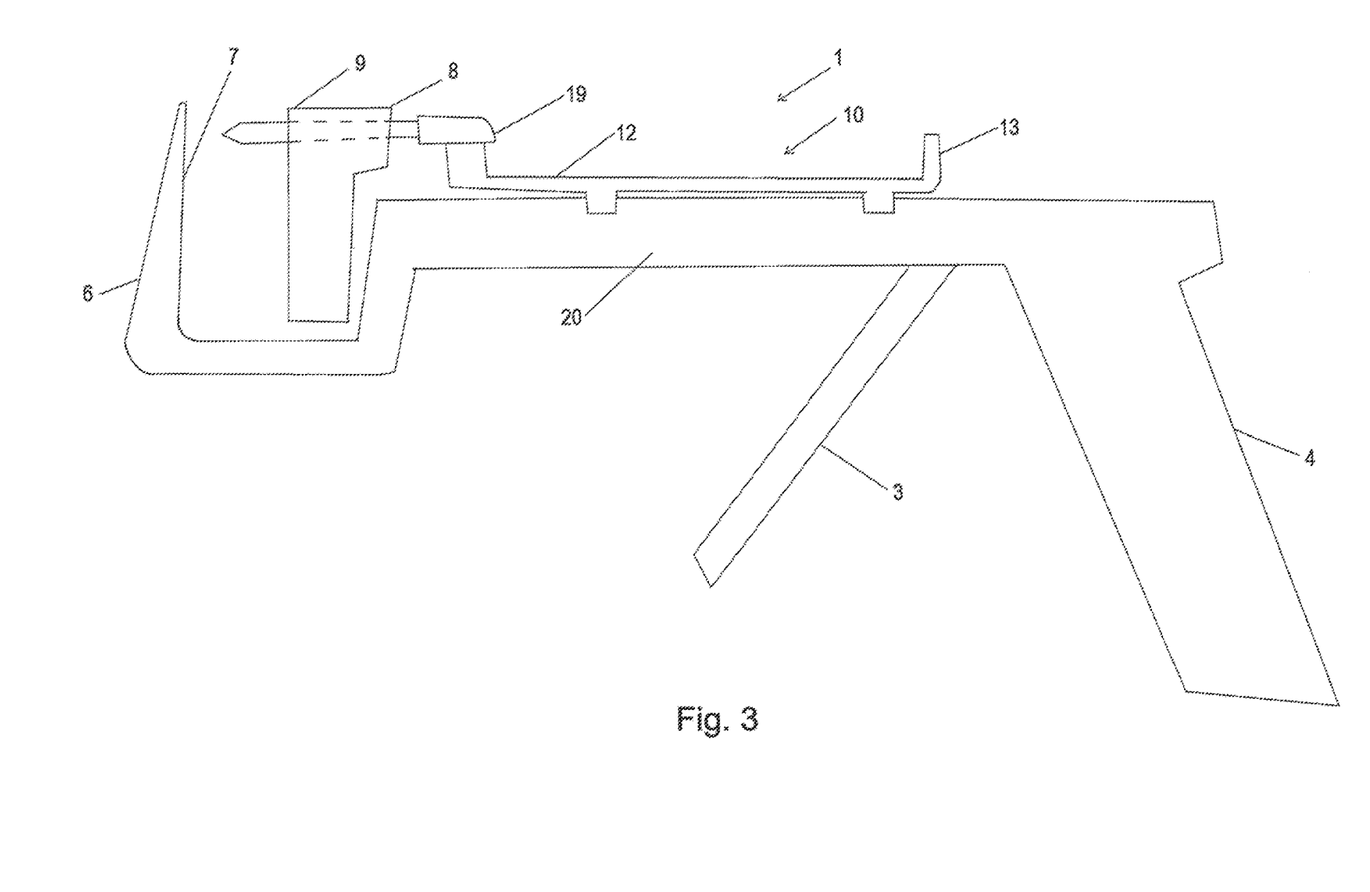
FIG. 3 is a schematic diagram of a linear stapler with a retaining pin subassembly in accordance with one exemplary embodiment of the present invention.

As shown in FIG. 3, the exemplary retaining pin subassembly 10 includes a retaining pin 11 with a connecting cover 12 extending therefrom. The connecting cover 12 may be a cover plate extending distally from a position near the proximate end of the linear stapler 1 and slidably covering on an opening above the left and right handle plates. The opening provides accessibility, for example, for placement and removal of parts that serve actuating functions, such that the linear stapler can be disassembled for cleaning. The width of the connecting cover 12 is sized to enable it to cross and almost across the left and right handle plates 2. During the insertion and firing of linear stapler 1, the connecting cover 12 closes the opening which would otherwise be expose to tissue as in the prior art instruments and therefore have a risk of tissue damage by trapping tissue therein. A base 19 for the retaining pin 11 is located on the distal end of the connecting cover 12. The retaining pin 11 extends distally from the base 19. As shown in FIG. 2, the cartridge 9 and the casing 16 each have a channeling hole 27, 43 through which the retaining pin 11 can extend. The distal end of the retaining pin 11 may be contained in the casing 16 and extend to anvil 7 by passing through the channeling holes 27, 43 on the casing 16 and cartridge 9. Correspondingly, a hole 71 can be formed on the anvil 7 for receiving the forwardmost end of the retaining pin 11, as shown in FIG. 1.

Figure 4:
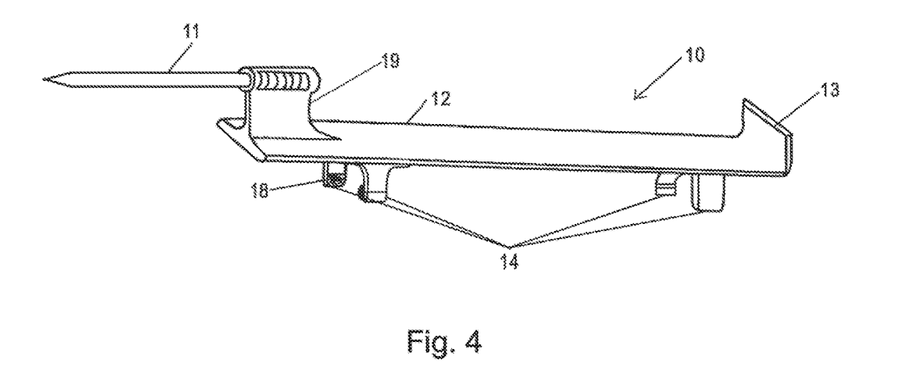
FIG. 4 is a perspective view of the retaining pin subassembly shown in FIG. 3.

The connecting cover 12 extends at an angle (e.g., about perpendicularly upwardly from the surface of the connecting cover 12) with its tail 13 at a proximate end to form an upstanding pushing lever 13 that a surgeon can manipulate manually. A force can be applied to the pushing lever 13 to move the connecting cover 12 and thereby the retaining pin 11 distally, until the retaining pin 11 reaches the anvil 7. The retaining pin 11 and connecting cover 12 are both reusable. They can be manufactured separately and assembled together. Alternatively, the retaining pin subassembly 10 can be formed integrally, such as by molding. The connecting cover 12 may be made of medical plastic and metal with suitable strength.

Preferably, two pairs of legs 14 extend downwardly from the bottom surface of the connecting cover 12 along its length and the retaining pin subassembly 10 is slidably supported on the handle stem 20 via these legs 14. In particular, two small bumps 18 may be formed on the surfaces of each pair of the legs 14 to face each other in the pair. For example, when the opposing inner surfaces of the legs 14 have a distance across the wide of the connecting cover 12 therebetween, bumps extending inwardly may be disposed in pairs on the inner surface of the legs 14. Preferably, the legs 14 may be elastic such that the connecting cover 12 can snap on the sides of the handle stem 20. Although a connecting cover 12 with two pairs of legs 14 and four bumps 18 is shown in the drawings, the number of legs and bumps may be varied. It can be understood that instead of the plurality of legs, a single continuing wall may be formed on each sides of the connecting cover 12 and each wall can be considered as a leg. Furthermore, the connecting cover 12 may be supported on the handle stem 20 in various ways, as long as it is slidable with respect to the handle stem 20.

The retaining pin subassembly 10 is movable between a retracted position and an extended position. In the retracted position, the forwardmost end of the retaining pin 11 passes through the channeling hole 43 on the casing 16 and the retaining pin 11 is located in the casing 16. Once the tissue to be sutured is positioned between the anvil 7 and the movable jaw 8, the pushing lever 13 is manipulated to move the retaining pin 11 distally. This causes the forwardmost end of the retaining pin 11 to pass through the channeling hole 27 in cartridge 9 and into the hole 71 on anvil 7, i.e., reach the extended position. In this extended position, the retaining pin 11 assures proper alignment of anvil 7 and cartridge 9 so that the staples will be properly aligned with the anvil pockets on the staple-forming surface of anvil 7 when the linear staple is fired. Furthermore, in this extended position, the retaining pin 11 spans the distance between the anvil 7 and cartridge 9, assuring that tissue located therebetween will remain therebetween during operation of the linear stapler 1.

Therefore, the retaining pin subassembly 10 achieves the cartridge alignment and tissue retention effectively. Besides, by employing the novel connecting cover 12 having the retaining pin 11 at its distal end, the retaining pin 11 does not have to extend from the proximate end up to the distal end of the linear stapler 1 as the conventional design does. Therefore, the retaining pin subassembly 10 will have higher strength and robustness compared to the prior art since the length of the slim pin/wire is significantly reduced and the pin 11 is supported by the connecting cover 12. Also, with the connecting cover 12 covering the opening between the handle stem 20, tissue damage for being trapped in the opening can be avoided without increasing the number of components.

As such, the retaining pin subassembly 10 is substantially improved in both structure and operability, which is of great importance to tissue stapling. However, a surgeon might sometimes forget to assemble the retaining pin subassembly, which will result in risks in performance of the device. Therefore, it is of great medical value to have a mechanism which can ensure a user such as a surgeon will not forget to assemble the retaining pin subassembly. Accordingly, the present invention preferably provides a locking device which ensures the retaining pin subassembly to be retained together with the handle stem so that the user will not miss the retaining pin subassembly during the reusable apparatus assembly process.

Figure 5:
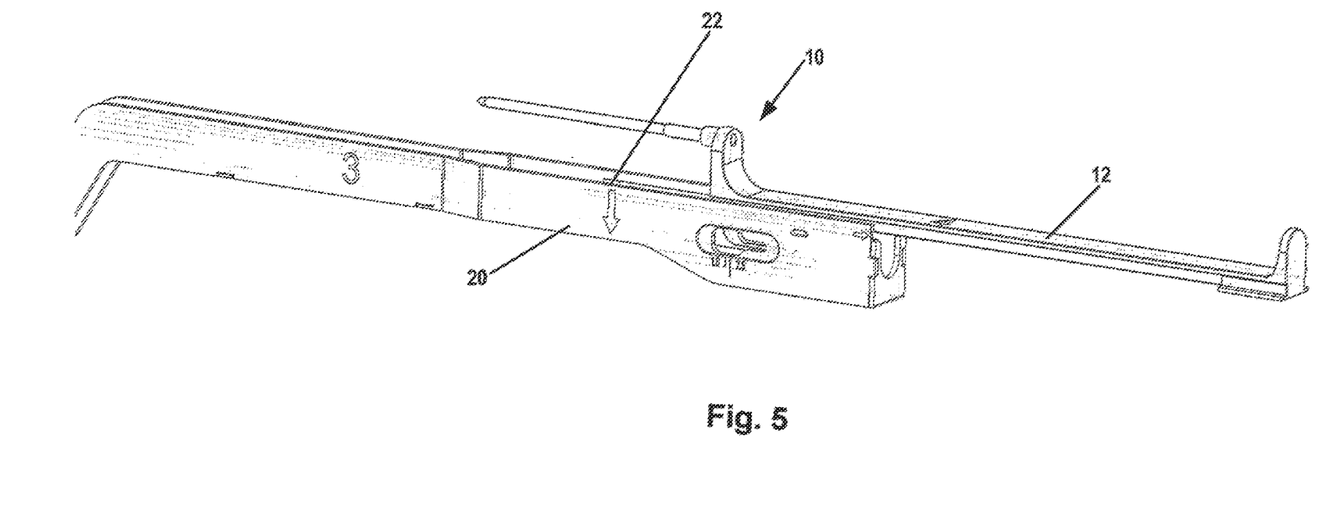
FIGS. 5-9 illustrate a locking device according to different embodiments of the present invention, respectively.

Specifically, as shown in FIG. 5, the connecting cover 12 can be pulled back to an end portion of the handle stem 20, and the connecting cover 12 cannot be disengaged from the handle stem 20. This can be achieved in various manners. For example, a recess 22 (only one recess is shown in the figure) is formed on the left and right handle plates, the connecting cover 12 is provided with a boss (not shown) which is slideable in the recess 22 and retains the connecting cover 22 and prevents it from disengaging from the handle stem 20.

Figure 6:
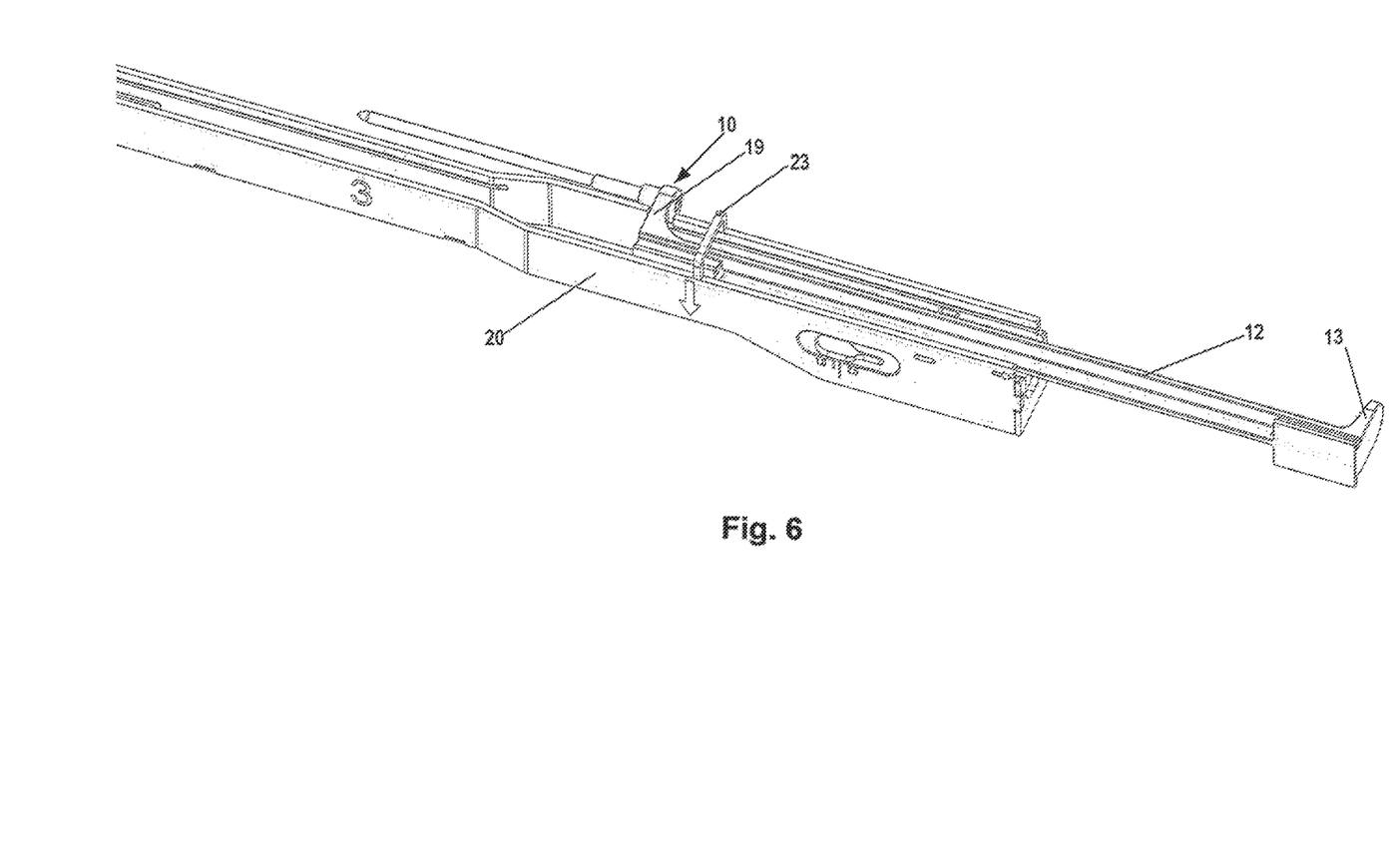

According to another embodiment, as shown in FIG. 6, a closed ring 23 is disposed on the handle stem 20 and sized so that the base 19 of the retaining pin subassembly 10 and the tail 13 cannot pass therethrough such that the retaining pin subassembly 10 cannot be disengaged from the handle stem 20. As shown in the figure, the retaining pin subassembly 10 can be turned 90 degrees and received in the opening of the handle stem 20, thereby forming a space for assembling other components such as a closure member.

Figure 7:
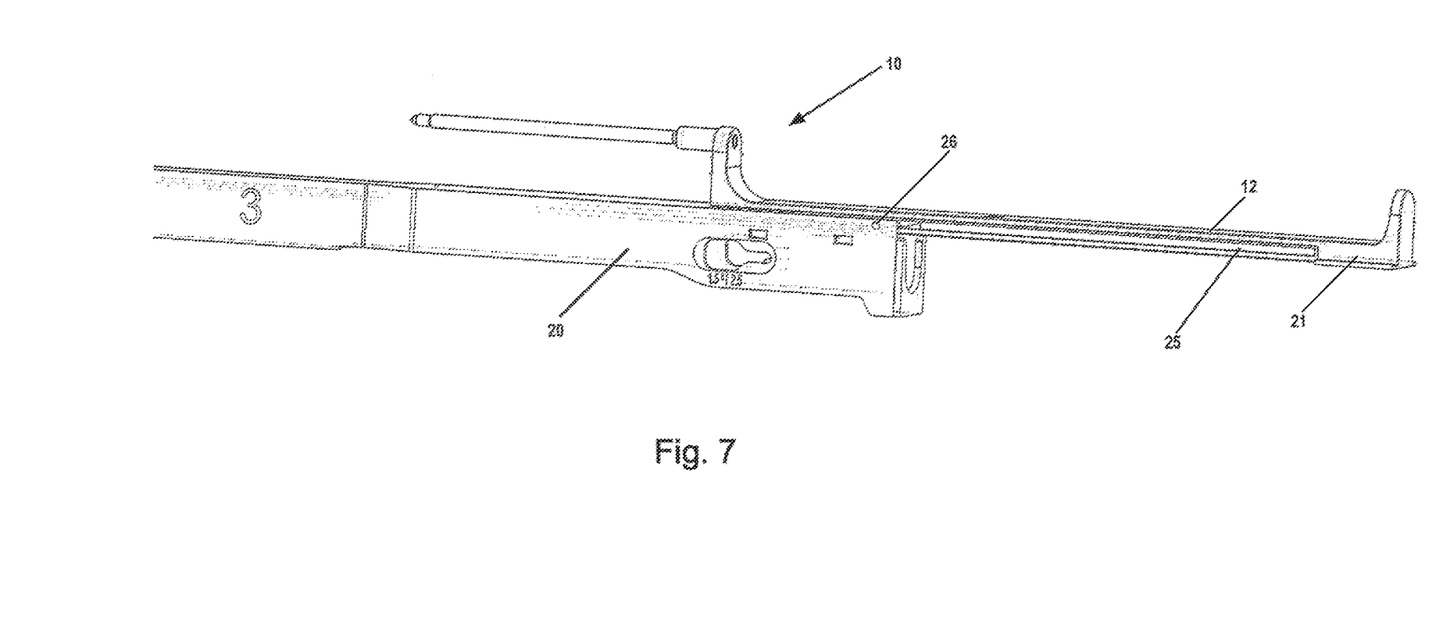

According to a further embodiment as shown in FIG. 7, a sidewall 21 is formed on both sides downwardly along a length of the connecting cover 12, a pair of grooves 25 are respectively formed on the sidewall 21 along the length, a through hole 26 is formed at the proximal end of the handle stem, a pin (not shown) passes through the through hole 26 in the handle stem and grooves 25 in the sidewall 21 to engage the handle stem 20 together with the retaining pin subassembly 10. It can be seen that through engagement of the pin and the grooves 25, the retaining pin assembly 10 is slideable on the handle stem 20 and rotatable about the pin. In this way, the retaining pin subassembly 10 and the handle stem 20 are locked together.

Figure 8:
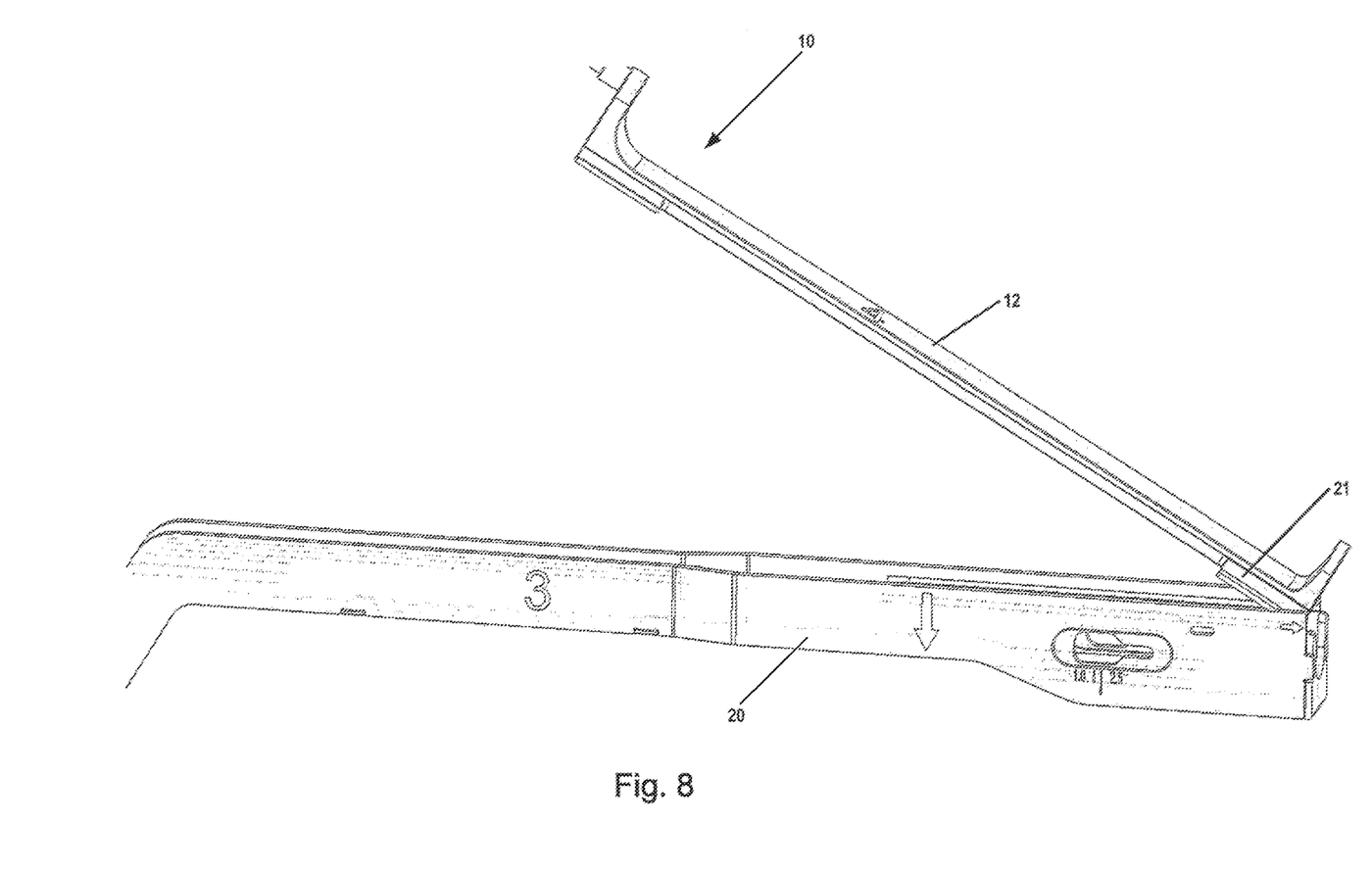

According to another embodiment as shown in FIG. 8, a bore allowing the pin to pass is formed on the proximal end of the sidewall 21 and the proximal end of the handle stem 20. The retaining pin subassembly 10 and handle stem 20 are connected together via the pin at the proximal ends. Furthermore, the retaining pin subassembly is wholly pivotal about the pin at said end, away from the handle stem 20 to open the opening of the handle stem 20 to expose the members received therein. At this time, the retaining pin 11 is set to be longitudinally moveable relative to the base 19. For example, the retaining pin 11 is connected to the base 19 through threaded engagement so that it can be screwed distally or proximally relative to the base 19.

Figure 9:
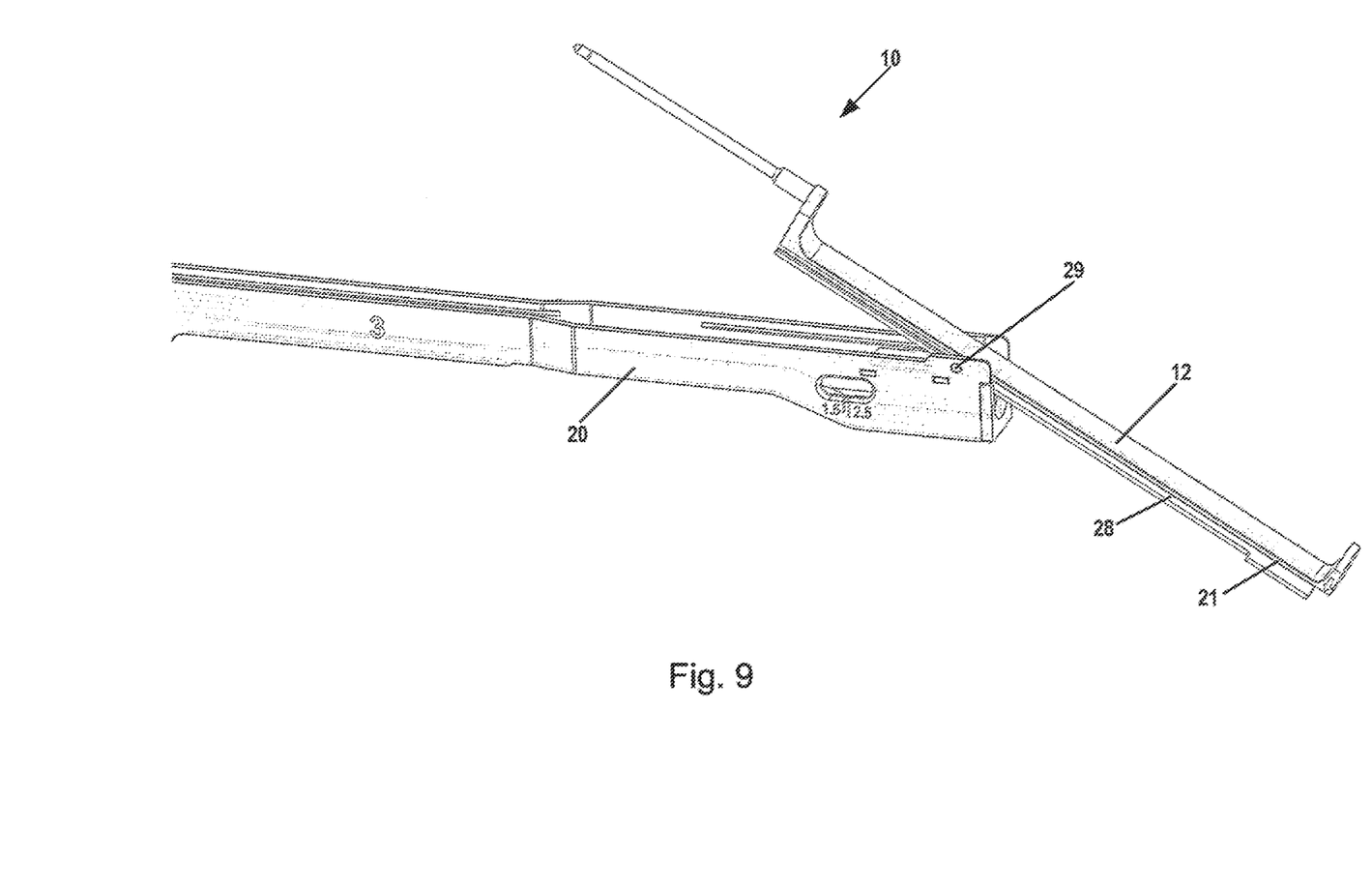

According to a further embodiment as shown in FIG. 9, instead of the grooves which are formed on the sidewall and are through the sidewall, non-through slots 28 may be formed on the two sidewalls along the length of the sidewall 21. A pair of through holes 29 is formed on for example proximal end of the handle stem, and two short pins (not shown) respectively retain the retaining pin subassembly 10 and the handle stem 20 together on both sides. In this way, the retaining pin subassembly 10 can be engaged in the slot 28 through the pin and slideable relative to the handle stem 20, and is rotatable about the pin as the rotation center relative to the handle stem 20.

Other variations, modifications and substitutions of the locking device will be apparent to those skilled in the art in view of the teachings herein.

The instruments disclosed herein can be designed to be disposed of after a single use, or they can be designed to be used multiple times. In either case, however, the instrument can be reconditioned for reuse after at least one use. Reconditioning can include any combination of the steps of disassembly of the instrument, followed by cleaning or replacement of particular pieces, and subsequent reassembly. In particular, the instrument can be disassembled, and any number of the particular pieces or parts of the instrument can be selectively replaced or removed in any combination. Upon cleaning and/or replacement of particular parts, the instrument can be reassembled for subsequent use either at a reconditioning facility, or by a surgical team immediately prior to a surgical procedure. Those skilled in the art will appreciate that reconditioning of an instrument can utilize a variety of techniques for disassembly, cleaning and/or replacement, and reassembly. Use of such techniques, and the resulting reconditioned instrument, are all within the scope of the present application. Furthermore, structures and methods of making such structures for cartridges, anvil, jaws, handle, actuating firing mechanism are within the knowledge of those skilled in the art.

Preferably, the invention described herein will be processed before surgery. Any suitable sterilization process can be used. First, a new or used instrument is obtained and if necessary cleaned. The instrument can then be sterilized. In one sterilization technique, as an example, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the principles and scope of the disclosure. This application is therefore intended to cover any variations, uses, or adaptations of the invention using its general principles. Further, this application is intended to cover such departures from the present disclosure within the known or customary practice in the art.

What is claimed is:

1. A linear stapler, comprising:
a body for supporting a cartridge having one or more surgical staples, wherein the body has a driver for acting on the cartridge to drive the surgical staples therefrom;
the body has a handle stem supporting an anvil against which tissue can be pressed by the cartridge for stapling; and
a retaining pin subassembly movably supported on the handle stem, wherein the retaining pin subassembly comprises a connecting cover and a retaining pin, the connecting cover being capable of covering an opening of the handle stem, the connecting cover comprising a base extending upwardly from a top portion of the connecting cover at its distal end and a tail or lever extending upwardly at its proximal end, the base being configured to receive a portion of the retaining pin such that the retaining pin extends distally therefrom and the tail or lever being configured to receive a force to enable movement of the retaining pin subassembly including the connecting cover and retaining pin longitudinally along the handle stem, the connecting cover further comprising a plurality of legs extending downwardly from the bottom portion of the connecting cover along a length thereof, at least a pair of the plurality of legs having bumps facing each other, the plurality of legs being configured to snap fit on to the handle stem via the bumps such that that the plurality of legs slidably support the retaining pin subassembly to the handle stem.

2. The linear stapler according to claim 1, wherein the retaining pin extends in a direction substantially parallel to the direction of slide of the connecting cover but is off set upward therefrom 1 cm to 10 cm.

3. The linear stapler according to claim 1, wherein the retaining pin extends in a direction aligned with a direction of slide of the connecting cover.

4. The linear stapler according to claim 1, wherein the tail or lever extends at an angle from a sliding direction of the connecting cover.

5. The linear stapler according to claim 1, wherein the connecting cover is made of a metal material.

6. The linear stapler according to claim 1, wherein the legs are elastic.

7. The linear stapler according to claim 1, wherein the handle stem includes left and right handle plates.

8. The linear stapler according to claim 1, wherein the retaining pin subassembly is undetachably connected to the handle stem via a locking device.

* * * * *